United States Patent
Izumi et al.

(10) Patent No.: US 9,522,917 B2
(45) Date of Patent: Dec. 20, 2016

(54) BRUTON'S TYROSINE KINASE INHIBITORS FOR HEMATOPOIETIC MOBILIZATION

(71) Applicant: Acerta Pharma B.V., Oss (NL)

(72) Inventors: Raquel Izumi, San Carlos, CA (US); Francisco Salva, San Francisco, CA (US); Ahmed Hamdy, Santa Cruz, CA (US)

(73) Assignee: Acerta Pharma B.V., Oss (NL)

( * ) Notice: Subject to any disclaimer, the term of this patent is extended or adjusted under 35 U.S.C. 154(b) by 0 days.

(21) Appl. No.: 14/394,061

(22) PCT Filed: Apr. 11, 2013

(86) PCT No.: PCT/US2013/036242
§ 371 (c)(1),
(2) Date: Oct. 10, 2014

(87) PCT Pub. No.: WO2013/155347
PCT Pub. Date: Oct. 17, 2013

(65) Prior Publication Data

US 2015/0086507 A1    Mar. 26, 2015

Related U.S. Application Data

(60) Provisional application No. 61/622,843, filed on Apr. 11, 2012.

(51) Int. Cl.
| | | |
|---|---|---|
| *C07D 487/04* | (2006.01) | |
| *A61K 45/06* | (2006.01) | |
| *C12N 5/0789* | (2010.01) | |
| *A61K 31/519* | (2006.01) | |
| *A61K 31/505* | (2006.01) | |

(52) U.S. Cl.
CPC .......... *C07D 487/04* (2013.01); *A61K 31/505* (2013.01); *A61K 31/519* (2013.01); *A61K 45/06* (2013.01); *C12N 5/0647* (2013.01)

(58) Field of Classification Search
USPC .... 424/85.2, 85.1, 93.7; 514/265.1; 435/325
See application file for complete search history.

(56) References Cited

U.S. PATENT DOCUMENTS

2009/0264339 A1*  10/2009  Yen .................. C07D 239/50
514/1.1

* cited by examiner

*Primary Examiner* — Kristin Vajda
(74) *Attorney, Agent, or Firm* — Morgan Lewis & Bockius LLP

(57) ABSTRACT

Methods to improve hematopoiesis and increase white blood cell counts in subjects and patients using pyrimidine-based inhibitors of Bruton's tyrosine kinase (Btk) are disclosed.

22 Claims, 1 Drawing Sheet

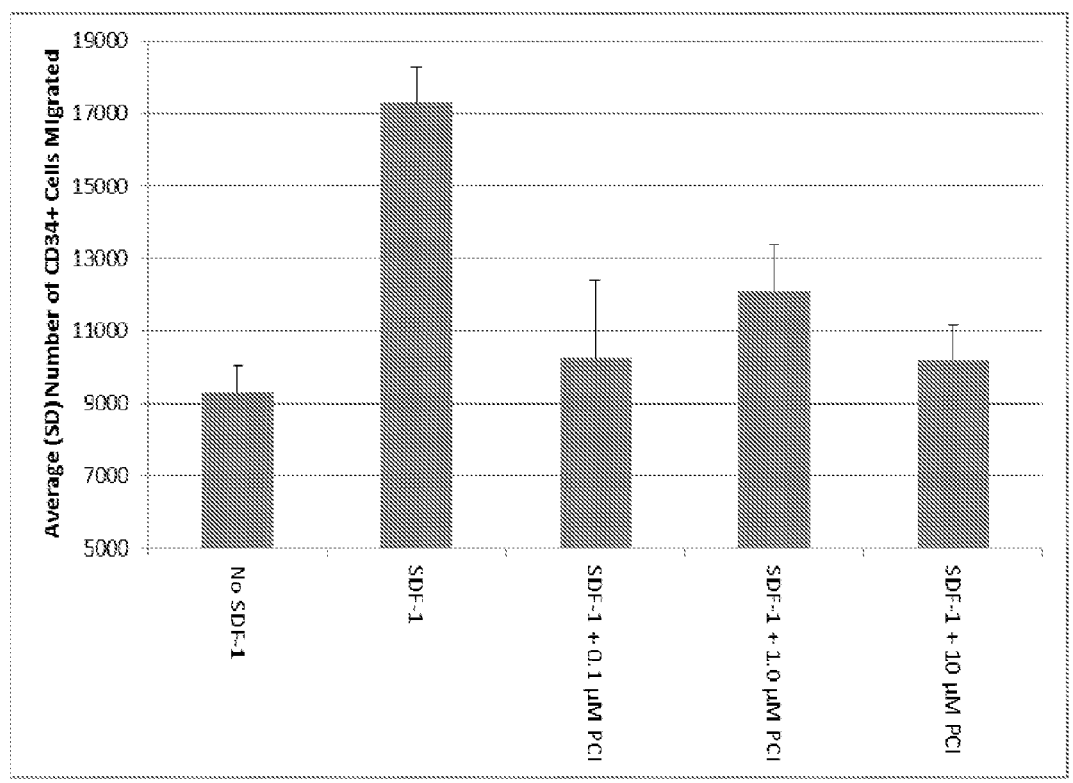

BRUTON'S TYROSINE KINASE INHIBITORS FOR HEMATOPOIETIC MOBILIZATION

CROSS-REFERENCE TO RELATED APPLICATIONS

This application is a continuation of International Patent Application No. PCT/US13/036242, filed Apr. 11, 2013, which in turn claims the benefit of U.S. Provisional Application Ser. No. 61/622,843, filed Apr. 11, 2012, entitled "BTK Inhibitors Capable of Mobilizing Progenitor Cells," each of which is incorporated by reference herein in its entirety.

FIELD OF INVENTION

The invention is in the field of therapeutics and medicinal chemistry. The present invention relates generally to the administration of a Bruton's tyrosine kinase inhibitor to mobilize hematopoietic stem and progenitor cells from the bone marrow into the peripheral blood and the use of such hematopoietic cells to improve hematopoiesis and/or in the treatment of various disorders.

BACKGROUND OF THE INVENTION

Bruton's tyrosine kinase (Btk) is a member of the Tec family of non-receptor tyrosine kinases and plays a role in several hematopoietic cell signaling pathways, e.g., Toll like receptor (TLR) and cytokine receptor-mediated TNF-$\alpha$ production in macrophages, IgE receptor (FcεRI) signaling in Mast cells, inhibition of Fas/APO-1 apoptotic signaling in B lineage lymphoid cells, and collagen-stimulated platelet aggregation. See, e.g., Jeffries, et al. (2003) *J. Biol. Chem.* 278:26258-26264; Horwood et al. (2003) *J. Exp. Med.* 197:1603-1611; Iwaki et al. (2005) *J. Biol. Chem.* 280(48): 40261-40270; Vassilev et al. (1999) *J. Biol. Chem.* 274(3): 1646-1656, and Quek et al. (1998), *Curr. Bio.* 8(20):1137-1140. It is a particularly important in the signaling pathway initiated upon stimulation of the B cell receptor and during B cell development. Mutations in the Btk gene result in X-linked agammaglobulinemia, an immunodeficiency characterized by failure to produce mature B lymphocytes and associated with a failure of Ig heavy chain rearrangement. Rawlings and Witte (1994) *Immun. Rev.* 138:105-119. In the mouse, point mutation or deletion of Btk causes X-linked immunodeficiency (xid), with about 50% fewer conventional B2 B cells, absent B1 B cells, and reduced serum Ig levels. Khan et al (1995) *Immunity* 3:283-99; Rawlings et al (1993) *Science* 261:358-61. Btk is also expressed in specific cells of the myeloid lineage, and evidence suggests that it contributes to immune-complex mediated activation of the FcγR and FcεR signaling pathways in monocytes/macrophages, neutrophils, and mast cells. See, e.g., Jongstra-Bilen et al. (2008) *J. Immunol.* 181:288-298; Wang et al. (2007) *Int. Immunopharmacol.* 7:541-546; Hata et al. (1998) *J Exp Med.* 187:1235-1247.

Due to the role of Btk in inhibiting Fas/APO-1 apoptotic signals in the B cell lineage, inhibitors of Btk, also referred to as Btk inhibitors, have been evaluated as agents for treating hematopoietic malignancies (e.g., B cell lymphoma). Additionally, due to the role of Btk in the signaling pathways of other immune cells, Btk inhibitors have also been evaluated as agents for suppressing the immune system, e.g., in patients with autoimmune disorders or organ transplants. See, e.g., Honinberg et al. (2010) *Proc. Natl. Acad. Sci. USA* 107:13075-80; Chang et al. (2011) *Arthr. Res. & Ther.* 13:R115. Evidence for the role of Btk in autoimmune and/or inflammatory disease has been established in Btk-deficient mouse models. For example, in standard murine preclinical models of systemic lupus erythematosus (SLE), Btk deficiency has been shown to result in a marked amelioration of disease progression. Moreover, Btk deficient mice are also resistant to developing collagen-induced arthritis and are less susceptible to *Staphylococcus*-induced arthritis Inhibition of Btk activity is useful for the treatment of autoimmune and/or inflammatory diseases such as: SLE, rheumatoid arthritis, multiple vasculitides, idiopathic thrombocytopenic purpura (ITP), myasthenia gravis, and asthma. See, e.g., U.S. Pat. No. 7,393,848.

Btk inhibitors have also been shown useful in preventing or reducing the risk of thromboembolism. See, e.g., Uckun (2008) *Int. Rev. Immunol.* 27:43-69.

SUMMARY OF INVENTION

In contrast to the prior art uses of Bruton's Tyrosine Kinase inhibitors to suppress immune cells and/or the immune system, disclosed herein is the surprising discovery that Btk inhibitors can mobilize hematopoietic stem cells and progenitor cells to the peripheral blood of a subject, e.g., to increase the white blood cell count in the subject. Accordingly, provided herein are methods and compositions for improving hematopoiesis and increasing the white blood cell count in a subject in need thereof, including patients undergoing chemotherapy, radiation therapy and/or bone marrow transplantation. Also provided herein are methods of determining whether a Btk inhibitor is a "mobilizing Btk inhibitor" capable of mobilizing hematopoietic stem and/or progenitor cells to the peripheral blood of a subject; and methods of using a mobilizing Btk inhibitor to mobilize such cells, including harvesting such cells for subsequent reinfusion into the same or a different subject.

In one aspect, the invention provides methods for mobilizing hematopoietic stem and/or progenitor cells in a subject in need thereof comprising administering to said subject a pharmaceutical composition comprising a mobilizing Bruton's Tyrosine Kinase (Btk) inhibitor in an amount effective to mobilize said cells into the peripheral blood of said subject. The inventive methods and uses can be advantageously employed in conjunction with bone marrow transplantation procedures, and/or subsequent to chemotherapy and/or radiation exposure to address leukopenia, neutropenia, granulocytopenia and/or thrombocytopenia in such patients. Accordingly, in some embodiments the subject may be a bone marrow transplantation patient, and/or a leukopenic or neutropenic patient or a patient at risk of impaired hematopoiesis due to prior chemotherapy and/or radiation therapy.

As compounds that increase the white blood cell count in a subject, the instant mobilizing Btk inhibitors may be administered as part of any therapeutic protocol aiming to restore or improve hematopoiesis in a patient in need thereof, e.g., to enhance the success of bone marrow transplantation, to reduce the extent or duration of leukopenia and neutropenia resulting from chemotherapy, radiation therapy or accidental radiation exposure, to enhance wound healing and burn treatment, and/or to aid in restoration of damaged organ tissue. They may also combat bacterial infections that are prevalent in leukemia.

In another aspect, the invention provides methods of obtaining mobilized hematopoietic stem and progenitor cells and uses thereof. The subject methods comprise administering to a subject a mobilizing Btk inhibitor in an amount effective to increase the number of such cells in the subject, preferably in the peripheral blood of the subject. In one embodiment, the administering step comprises administration of a mobilizing Btk inhibitor alone. In another embodiment, the step comprises administration of a mobilizing Btk inhibitor in combination with other compounds, e.g., cytokines, that also increase the white blood cell count in the peripheral blood of a subject. Suitable compounds may be selected from the group consisting of granulocyte-macrophage colony stimulating factor (GM-CSF), Interleukin-1 (IL-1), Interleukin-3 (IL-3), Interleukin-8 (IL-8), PIXY-321 (GM-CSF/IL-3 fusion protein), macrophage inflammatory protein, stem cell factor, plerixafor, thrombopoietin, growth related oncogene, and/or combinations thereof. Thus, the subject methods comprise administering to a subject a mobilizing Btk inhibitor (with or without other mobilizing factors) in an amount effective to increase the number of hematopoietic stem and progenitor and/or white blood cells in the peripheral blood of the subject, and obtaining the immune cells so mobilized, e.g., by apheresis.

The harvested cells may be used therapeutically, e.g., in hematopoietic stem and/or progenitor cell transplantation. Accordingly, in another aspect the invention provides methods of treating a patient in need of improved hematopoiesis comprising administering to a subject a mobilizing Btk inhibitor (with or without other mobilizing factors) in an amount effective to increase the number of hematopoietic stem, progenitor and/or white blood cells in the peripheral blood of the subject, obtaining the cells so mobilized, and introducing the cells into the patient. Preferably, the subject and the patient are histocompatible. In one embodiment, the histocompatible subject and the patient are syngeneic. In another embodiment, the histocompatible subject and the patient are allogeneic.

In another embodiment, the harvested cells are enriched and/or cultured ex vivo prior to introduction into the patient. Such ex vivo culture comprises differentiating the obtained cells into or enriching for myeloid cells, lymphoid cells, and common progenitors thereof etc. Accordingly, in one embodiment, a method of treating a patient in need thereof further comprises culturing the obtained hematopoietic cells in one or more differentiation factors prior and/or enriching the obtained hematopoietic cells for a common progenitor cell or cells prior to introducing the cells into the patient.

Mobilizing Btk inhibitors may be administered to any animal subject in order to mobilize hematopoietic stem and progenitor cells. In a preferred embodiment, the mobilizing Btk inhibitor is administered to a mammal, and more preferably to a human.

Preferred mobilizing Btk inhibitors suitable for use in the subject invention comprise a pyrimidine ring, i.e., a 1,3 diazine. In one embodiment, the mobilizing Btk inhibitor is selected from a compound of structural Formula I:

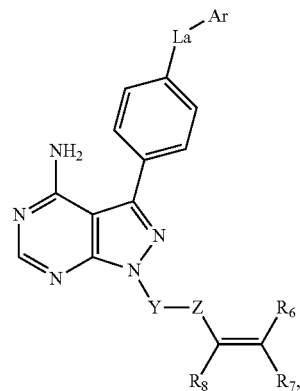

wherein:

La is $CH_2$, O, NH or S;

Ar is a substituted or unsubstituted aryl, unsubstituted phenyl, or a substituted or unsubstituted heteroaryl;

Y is a 4-, 5-, 6-, or 7-membered cycloalkyl ring, or

Y is a 4-, 5-, 6-, or 7-membered monocyclic nitrogen containing heterocycloalkyl ring; or Y is an optionally substituted group selected from among alkyl, heteroalkyl, cycloalkyl, heterocycloalkyl, aryl, and heteroaryl; or Y is selected form the group consisting of azetidinyl, pyrrolidinyl, piperidinyl, and azepanyl;

Z is $C(=O)$, $OC(=O)$, $NHC(=O)$, $NRC(=O)$, $C(=S)$, $S(=O)x$, $OS(=O)_x$, $NHS(=O)x$, where x is 1 or 2;

$R_7$ and $R_8$ are independently selected from among H, unsubstituted $C_1$-$C_4$alkyl, substituted $C_1$-$C_4$ alkyl, $C_1$-$C_6$ alkoxyalkyl, $C_1$-$C_8$ alkylamino alkyl, $C_1$-$C_4$ alkyl(phenyl), unsubstituted $C_1$-$C_4$heteroalkyl, substituted $C_1$-$C_4$heteroalkyl, unsubstituted $C_3$-$C_6$cycloalkyl, substituted $C_3$-$C_6$cycloalkyl, unsubstituted $C_2$-$C_6$heterocycloalkyl, and substituted $C_2$-$C_6$heterocycloalkyl; or $R_7$ and $R_8$ taken together form a bond;

$R_6$ is H, substituted or unsubstituted $C_1$-$C_4$alkyl, substituted or unsubstituted $C_1$-$C_4$heteroalkyl, $C_1$-$C_6$alkoxyalkyl, $C_1$-$C_8$alkylaminoalkyl, substituted or unsubstituted $C_3$-$C_6$cycloalkyl, substituted or unsubstituted aryl, substituted or unsubstituted $C_2$-$C_8$heterocycloalkyl, substituted or unsubstituted heteroaryl, $C_1$-$C_4$alkyl(aryl), $C_1$-$C_4$alkyl(phenyl), $C_1$-$C_4$alkyl(heteroaryl), $C_1$-$C_4$alkyl($C_3$-$C_8$cycloalkyl), or $C_1$-$C_4$alkyl($C_2$-$C_8$heterocycloalkyl), or $C_1$-$C_8$ alkylamino alkyl;

R is H, or $C_1$-$C_6$alkyl; and pharmaceutically acceptable solvates or pharmaceutically acceptable salts thereof.

In another embodiment, the mobilizing Btk inhibitor for use in the subject invention is selected from a compound of structural Formula II:

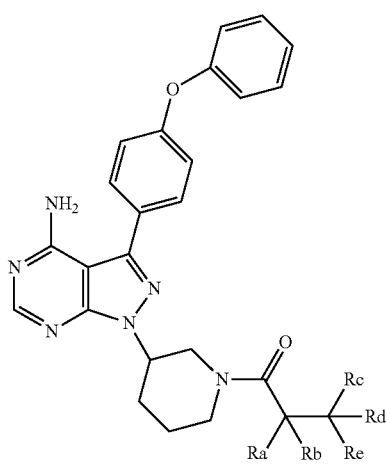

wherein:

Ra, Rb, Rc, Rd, and Re, are each independently selected from H, F, Cl, Br, I, —CN, —SR$_2$, —OR$_3$, CO$_2$R$_3$; or Ra, or Rb together with one of Rc, Rd and Re, and the carbon atoms to which they are attached form an epoxide; wherein Ra, Rb, Rc, Rd, and Re, cannot all be H;

R$_2$ is selected from H, methyl, ethyl, n-propyl, iso-propyl, n-butyl, iso-butyl, tert-butyl, a cysteinyl, a glutathionyl, C$_1$-C$_4$alkyl, a cysteinyl, or a glutathionyl;

R$_3$ is selected from H, C$_1$-C$_4$alkyl, phenyl, or benzyl; and pharmaceutically acceptable solvates or pharmaceutically acceptable salts thereof.

In another embodiment, the mobilizing Btk inhibitor for use in the subject invention is selected from a compound of structural Formula III:

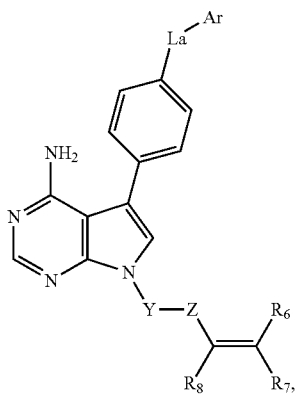

wherein;

La is O or S;

Ar is an unsubstituted phenyl;

Y is a 4-, 5-, 6-, or 7-membered cycloalkyl ring, or

Y is a 4-, 5-, 6-, or 7-membered monocyclic nitrogen containing heterocyclic ring;

Z is C(=O), OC(=O), NHC(=O), S(=O)$_x$, or NHS(=O)$_x$, where x is 2;

R$_8$ is H; R$_7$ is H, unsubstituted C$_1$-C$_4$ alkyl, C$_1$-C$_6$ alkoxyalkyl, C$_1$-C$_8$ alkylaminoalkyl, or C$_1$-C$_4$ alkyl(phenyl); or R$_7$ and R$_8$ taken together form a bond;

R$_6$ is H, unsubstituted C$_1$-C$_4$ alkyl, C$_1$-C$_6$ alkoxyalkyl, C$_1$-C$_8$ alkylaminoalkyl, or C$_1$-C$_4$ alkyl(phenyl); and pharmaceutically acceptable solvates or pharmaceutically acceptable salts thereof.

In certain embodiments, the compounds of Formulas I-III may include an asymmetric center or centers, and may be in the form of a composition of a racemic mixture, a diastereoisomeric mixture, a single enantiomer, an enantiomeric diastereomer, a meso compound, a pure epimer, or a mixture of epimers thereof, etc. Further, the compounds of Formulas I or II may have one or more double bonds, and may be in a form of a cis/trans, E/Z mixture or an E or Z geometric isomer thereof.

The compounds of Formulas I, II and III may also be prepared as a salt form, e.g., pharmaceutically acceptable salts, including suitable acid forms, e.g., salt forms selected from hydrochloride, hydrobromide, acetate, propionate, butyrate, sulphate, hydrogen sulphate, sulphite, carbonate, hydrogen carbonate, phosphate, phosphinate, oxalate, hemi-oxalate, malonate, hemi-malonate, fumarate, hemi-fumarate, maleate, hemi-maleate, citrate, hemi-citrate, tartrate, hemi-tartrate, aspartate, glutamate, etc.

BRIEF DESCRIPTION OF THE FIGURES

FIG. 1 shows the results of an in vitro transwell assay using human CD34$^+$ cells and migration towards an SDF-1 gradient with varying concentrations of a pyrimidine-based Btk inhibitor.

DETAILED DESCRIPTION

Blood cells play a crucial part in maintaining the health and viability of animals, including humans. White blood cells include neutrophils, macrophages, eosinophils, basophils, mast cells, and the B and T cells of the immune system. White blood cells are continuously replaced via the hematopoietic system, by the action of colony stimulating factors (CSF) and various cytokines on progenitor cells in hematopoietic tissues. The nucleotide sequences encoding a number of these growth factors have been cloned and sequenced. Perhaps the most widely known of these is granulocyte colony stimulating factor (G-CSF) which has been approved for use in counteracting the negative effects of chemotherapy by stimulating the production of white blood cells and progenitor cells (peripheral blood stem cell mobilization). A discussion of the hematopoietic effects of this factor can be found, for example, in U.S. Pat. No. 5,582,823, incorporated herein by reference.

Several other factors have been reported to increase white blood cells and progenitor cells in both human and animal subjects. These agents include granulocyte-macrophage colony stimulating factor (GM-CSF), Interleukin-1 (IL-1), Interleukin-3 (IL-3), Interleukin-8 (IL-8), PIXY-321 (GM-CSF/IL-3 fusion protein), macrophage inflammatory protein, stem cell factor, thrombopoietin and growth related oncogene, as single agents or in combination. Dale et al. (1998) *Am. J. of Hematol.* 57:7-15; Rosenfeld et al. (1997) *Bone Marrow Transplantation* 17:179-183; Pruijt et al., (1999) *Cur. Op. in Hematol.* 6:152-158; Broxmeye et al. (1995) *Exp. Hematol.* 23:335-340; Broxmeyer et al. (1998) *Blood Cells, Molecules and Diseases* 24:14-30; Glaspy et al. (1996) *Cancer Chemother. Pharmacol.* 38 (suppl): S53-S57; Vadhan-Raj et al. (1997) *Ann. Intern. Med.* 126:673-81; King et al. (2001) *Blood* 97:1534-1542; Glaspy et al. (1997) *Blood* 90:2939-2951.

While endogenous growth factors are pharmacologically effective, the well-known disadvantages of employing proteins and peptides as pharmaceuticals underlies the need to add to the repertoire of such growth factors with agents that are small molecules. In another aspect, such small molecules are advantageous over proteins and peptides where production in large quantities are desired.

As used herein, the term "progenitor cell" refers to a cell that, in response to certain stimuli, can form differentiated hematopoietic or myeloid cells. The presence of progenitor cells can be assessed by the ability of the cells in a sample to form colony-forming units of various types, including, for example, CFU-GM (colony-forming units, granulocyte-macrophage); CFU-GEMM (colony-forming units, multipotential); BFU-E (burst-forming units, erythroid); HPP-CFC (high proliferative potential colony-forming cells); or other types of differentiated colonies which can be obtained in culture using known protocols.

As used herein, "stem cells" are less differentiated forms of progenitor cells. Typically, such cells are often positive for CD34. Some stem cells do not contain this marker, however. These CD34+ cells can be assayed using fluorescence activated cell sorting (FACS) and thus their presence can be assessed in a sample using this technique.

In general, CD34+ cells are present only in low levels in the blood, but are present in large numbers in bone marrow. While other types of cells such as endothelial cells and mast cells also may exhibit this marker, CD34 is considered an index of stem cell presence.

The development and maturation of blood cells is a complex process. Mature blood cells are derived from hematopoietic precursor cells (progenitor) cells and stem cells present in specific hematopoietic tissues including bone marrow. Within these environments hematopoietic cells proliferate and differentiate prior to entering the circulation. The chemokine receptor CXCR4 and its natural ligand stromal cell derived factor-1 (SDF-1) appear to be important in this process. See, e.g., Maekawa et al (2000) *Internal Med.* 39:90-100; Nagasawa et al. (2000) *Int. J. Hematol.* 72:408 411). This is demonstrated by reports that CXCR4 or SDF-1 knock-out mice exhibit hematopoietic defects. Ma et al. (1998) *Proc. Natl. Acad. Sci. USA* 95:9448 9453; Tachibana et al. (1998) Nature 393:591 594; Zou et al. (1998) *Nature* 393:595-599.

It is also known that CD34+ progenitor cells express CXCR4 and require SDF-1 produced by bone marrow stromal cells for chemoattraction and engraftment, Peled et al. (1999) *Science* 283:845-48, and that in vitro, SDF-1 is chemotactic for both CD34+ cells, Aiuti et al. (1997) *J. Exp. Med.* 185:111-120; Viardot et al. (1998) *Ann. Hematol.* 77:194 197, and for progenitor cells, Jo et al. (2000) *J. Clin. Invest.* 105:101-111. SDF-1 is also an important chemoattractant, signaling via the CXCR4 receptor, for several other more committed hematopoietic progenitors and mature blood cells including T-lymphocytes and monocytes, Bleul et al. (1996) *J. Exp. Med.* 184:1101-1109), pro- and pre-B lymphocytes, Fedyk et al. (1999) *J. Leukoc. Biol.* (1999) 66:667-673; Ma et al. (1999) *Immunity* 10:463-71, and megakaryocytes. Hodohara et al. (2000) *Blood* 95:769-75; Riviere et al. (1999) *Blood* 95:1511-23; Majk et al. (2000) *Blood* 96:4142-51; Gear et al. (2001) *Blood* 97:937-45; Abi-Younes et al. (2000) *Circ. Res.* 86:131-38.

The SDF-1/CXCR4 signaling axis is known to direct homing and engraftment of hematopoietic stem cells to the bone marrow. Kucia et al. (2005) *Stem Cells* 23:879-94. SDF-1 is a CXC chemokine and is considered as one of the most potent chemoattractants of hematopoietic stem cells (HSC) into the bone marrow. Lapid et al (2009) "Egress and Mobilization of Hematopoietic Stem and Progenitor Cells" in StemBook (available at www.stembook.org/node/558).

SDF-1 binding to CXCR4 triggers G protein coupling (from inactive conformation to an active conformation) and subsequent dissociation of the heterotrimeric G protein into Gβγ and Gαi subunits, which in turn bind to several downstream effectors, resulting in activation of PI3K, protein kinase C (PKC), and MAPK-mediated pathways. Sharma et al. (2011) *Stem Cells Dev.* 20 (6): 933-46. Studies of the SDF 1/CXCR4 axis in B-cell migration have identified Bruton's tyrosine kinase (Btk) as a central kinase in the SDF-1/ CXCR4 signaling cascade. De Gorter et al. (2007) *Immunity* 26: 93-104. Btk expression has been described in HSC, multipotent progenitor cells and cells of the myeloid lineage, Mohammed et al. (2009) *Immunological Reviews* 228: 58-73, including erythroid cells, platelets, monocytes, macrophages, granulocytes, and dendritic cells. In the lymphoid lineage, Btk is expressed in B cells, but not in T cells or natural killer cells (NK cells). Schmidt et al (2004) *Int Arch Allergy Immunol.* 134:65-78.

Notably, blocking of the SDF-1/CXCR4 signaling axis by AMD3100 (plerixafor or Mozobil®), a small molecule inhibitor which binds to CXCR4 preventing binding of SDF-1 and subsequent downstream signaling, causes rapid and reversible mobilization of CD34+ HSC into the peripheral blood for harvesting by apheresis. Blocking the SDF-1/CXCR4 signaling cascade with a Btk inhibitor (PCI-32765) in patients with B-cell malignancies produces rapid and clinically significant decreases in lymphadenopathy as the malignant B cells are mobilized out of the lymph nodes and into the peripheral blood producing a marked lymphocytosis. The present invention elucidates the role of Btk in HSC homing and mobilization and provides compositions and methods of using Btk inhibitors for hematopoietic stem and/or progenitor cell mobilization.

Definitions

"Alkyl" means a straight or branched chain, saturated monovalent hydrocarbon radical. By way of example, the hydrocarbon chain may have from one to twenty carbons, one to sixteen carbons, one to fourteen carbons, one to twelve carbons, one to ten carbons, one to eight carbons, one to six carbons, one to four carbons, etc. "Lower alkyl" may refer to alkyls having, e.g., one to six carbons, one to four carbons, etc. In certain examples, an straight chain alkyl may have from one to six carbon atoms and a branched alkyl three to six carbon atoms, e.g., methyl, ethyl, propyl, 2-propyl, butyl (including all isomeric forms), pentyl (including all isomeric forms), and the like. "Me" means methyl, "Et" means ethyl, and "iPr" means isopropyl.

"Aryl" means a monovalent monocyclic or bicyclic aromatic hydrocarbon radical, e.g., having from of 6 to 20 or 6 to 10 ring atoms e.g., phenyl or naphthyl.

"Alkylaryl" means a (alkylene)-R radical where R is aryl as defined above.

"Cycloalkyl" means a cyclic saturated or partially saturated monovalent hydrocarbon radical (or an alicyclic radical). By way of example, the cycloalkyl may have from three to twenty carbon atoms, from three to sixteen carbon atoms, from three to fourteen carbon atoms, from three to twelve carbon atoms, from three to ten carbon atoms, from three to eight carbon atoms, from three to six carbon atoms, etc., wherein one or two carbon atoms may be replaced by an oxo group, e.g., admantanyl, cyclopropyl, cyclobutyl, cyclopentyl, cyclohexyl, cyclohexenyl, indanyl and the like.

"Alkylcycloalkyl" means a (alkylene)-R radical where R is cycloalkyl as defined above; e.g., cyclopropylmethyl, cyclobutylmethyl, cyclopentylethyl, or cyclohexylmethyl, and the like.

"Heterocyclyl" or "heterocycloalkyl" means a saturated or unsaturated monovalent monocyclic group, in which one or two ring atoms are heteroatom selected from N, O, or S, the remaining ring atoms being C. The heterocyclyl ring is optionally fused to a (one) aryl or heteroaryl ring as defined herein. The heterocyclyl ring fused to monocyclic aryl or heteroaryl ring is also referred to in this Application as "bicyclic heterocyclyl" ring. Additionally, one or two ring carbon atoms in the heterocyclyl ring can optionally be replaced by a —CO— group. More specifically the term heterocyclyl includes, but is not limited to, pyrrolidino, piperidino, homopiperidino, 2-oxopyrrolidinyl, 2-oxopiperidinyl, morpholino, piperazino, tetrahydropyranyl, thiomorpholino, and the like. When the heterocyclyl ring is unsaturated it can contain one or two ring double bonds. When the heterocyclyl group contains at least one nitrogen atom, it is also referred to herein as heterocycloamino and is a subset of the heterocyclyl group. When the heterocyclyl group is a saturated ring and is not fused to aryl or heteroaryl ring as stated above, it is also referred to herein as saturated monocyclic heterocyclyl.

"Alkylheterocycloalkyl" means a-(alkylene)-R radical where R is heterocyclyl ring as defined above e.g., tetrahydrofuranylmethyl, piperazinylmethyl, morpholinylethyl, and the like.

"Heteroaryl" means a monovalent monocyclic or bicyclic aromatic radical, where one or more, preferably one, two, or three, ring atoms are heteroatom selected from N, O, or S, the remaining ring atoms being carbon. Representative examples include, but are not limited to, pyrrolyl, thienyl, thiazolyl, imidazolyl, furanyl, indolyl, isoindolyl, oxazolyl, isoxazolyl, diazolyl, pyrazolyl, triazolyl, benzothiazolyl, benzoxazolyl, quinolinyl, isoquinolinyl, pyridinyl, pyrimidinyl, pyrazinyl, pyridazinyl, tetrazolyl, and the like.

"Oxo" or "carbonyl" means =(O) group or C=O group, respectively.

The term "substituted" means that the referenced group is substituted with one or more additional group(s) individually and independently selected from groups described herein. In some embodiments, an optional substituent is selected from oxo, halogen, —CN, —NH$_2$, —OH, —NH(CH$_3$), —N(CH$_3$)$_2$, alkyl (including straight chain, branched and/or unsaturated alkyl), substituted or unsubstituted cycloalkyl, substituted or unsubstituted heterocycloalkyl, fluoroalkyl, substituted or unsubstituted heteroalkyl, substituted or unsubstituted alkoxy, fluoroalkoxy, —S-alkyl, —S(O)$_2$-alkyl, —CONH((substituted or unsubstituted alkyl) or (substituted or unsubstituted phenyl)), —CON(H or alkyl)$_2$, —OCON(substituted or unsubstituted alkyl)$_2$, —NHCONH ((substituted or unsubstituted alkyl) or (substituted or unsubstituted phenyl)), —NHCOalkyl, —N(substituted or unsubstituted alkyl)CO(substituted or unsubstituted alkyl), —NHCOO (substituted or unsubstituted alkyl), —C(OH)(substituted or unsubstituted alkyl)$_2$, and —C(NH$_2$)(substituted or unsubstituted alkyl)$_2$. In some embodiments, by way of example, an optional substituent is selected from oxo, fluorine, chlorine, bromine, iodine, —CN, —NH$_2$, —OH, —NH(CH$_3$), —N(CH$_3$)$_2$, —CH$_3$, —CH$_2$CH$_3$, —CH(CH$_3$)$_2$, —CF$_3$, —CH$_2$CF$_3$, —OCH$_3$, —OCH$_2$CH$_3$, —OCH(CH$_3$)$_2$, —OCF$_3$, —OCH$_2$CF$_3$, —S(O)$_2$—CH$_3$, —CONH$_2$, —CONHCH$_3$, —NHCONHCH$_3$, —COCH$_3$, —COOH and the like. In some embodiments, substituted groups are substituted with one, two or three of the preceding groups. In some embodiments, substituted groups are substituted with one or two of the preceding groups. In some embodiments, substituted groups are substituted with one of the preceding groups. Further, unless stated to the contrary, a formula with chemical bonds shown only as solid lines and not as wedges or dashed lines contemplates each possible isomer, e.g., each enantiomer and diastereomer, and a mixture of isomers, such as racemic or scalemic mixtures.

The term "amino acid" includes any one of the twenty naturally-occurring amino acids or the D-form of any one of the naturally-occurring amino acids. In addition, the term "amino acid" also includes other non-naturally occurring amino acids besides the D-amino acids, which are functional equivalents of the naturally-occurring amino acids. Such non-naturally-occurring amino acids include, for example, norleucine ("Nle"), norvaline ("Nva"), L- or D-naphthalanine, ornithine ("Orn"), homoarginine (homoArg) and others well known in the peptide art, such as those described in M. Bodanzsky, "Principles of Peptide Synthesis," 1st and 2nd Revised Ed., Springer-Verlag, New York, N.Y., 1984 and 1993, and Stewart and Young, "Solid Phase Peptide Synthesis," 2nd Ed., Pierce Chemical Co., Rockford, Ill., 1984, both of which are incorporated herein by reference.

Amino acids and amino acid analogs can be purchased commercially (Sigma Chemical Co.; Advanced Chemtech) or synthesized using methods known in the art.

"Therapeutically effective amount" or "effective amount" means the amount of a composition, compound, therapy, or course of treatment that, when administered to a subject for treating a disease, disorder, or condition, is sufficient to effect such treatment for the disease, disorder, or condition. The "therapeutically effective amount" will vary depending on the composition, the compound, the therapy, the course of treatment, the disease, disorder, or condition, and its severity and the age, weight, etc., of the subject to be treated.

Btk Inhibitors

Bruton's tyrosine kinase is a member of the cytoplasmic Tec family of kinases. Like other Btk family members, it contains a pleckstrin homology (PH) domain, and Src homology SH3 and SH2 domains. Btk plays an important role in B cell development. Btk comprises of several domains from the N-terminus: the PH, Tec homology (TH), SH2, SH3, and kinase (SH1) domains. Each of these domains has the potential to interact with a plethora of proteins critical for intracellular signaling. Moreover, functional association of Btk with many of its partners is crucial for its activation and regulation. Btk is a metalloprotein enzyme requiring Zn2+ for optimal activity and stability. Mohammed (2009) *Immuno. Rev.* 228:58-73.

Preferred mobilizing Btk inhibitors suitable for use in the subject invention comprise a pyrimidine ring, i.e. a 1,3 diazine. In one embodiment, the mobilizing Btk inhibitor is selected from a compound of structural Formula I:

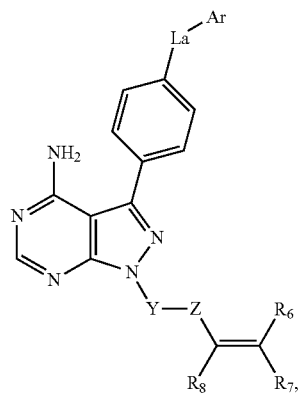

wherein:

La is $CH_2$, O, NH or S;

Ar is a substituted or unsubstituted aryl, unsubstituted phenyl, or a substituted or unsubstituted heteroaryl;

Y is a 4-, 5-, 6-, or 7-membered cycloalkyl ring, or

Y is a 4-, 5-, 6-, or 7-membered monocyclic nitrogen containing heterocycloalkyl ring; or Y is an optionally substituted group selected from among alkyl, heteroalkyl, cycloalkyl, heterocycloalkyl, aryl, and heteroaryl; or Y is selected form the group consisting of azetidinyl, pyrrolidinyl, piperidinyl, and azepanyl;

Z is C(=O), OC(=O), NHC(=O), NRC(=O), C(=S), S(=O)x, OS(=O)$_x$, NHS(=O)x, where x is 1 or 2;

$R_7$ and $R_8$ are independently selected from among H, unsubstituted $C_1$-$C_4$alkyl, substituted $C_1$-$C_4$alkyl, $C_1$-$C_6$alkoxyalkyl, $C_1$-$C_8$alkylamino alkyl, $C_1$-$C_4$alkyl(phenyl), unsubstituted $C_1$-$C_4$heteroalkyl, substituted $C_1$-$C_4$heteroalkyl, unsubstituted $C_3$-$C_6$cycloalkyl, substituted $C_3$-$C_6$cycloalkyl, unsubstituted $C_2$-$C_6$heterocycloalkyl, and substituted $C_2$-$C_6$heterocycloalkyl; or $R_7$ and $R_8$ taken together form a bond;

$R_6$ is H, substituted or unsubstituted $C_1$-$C_4$alkyl, substituted or unsubstituted $C_1$-$C_4$heteroalkyl, $C_1$-$C_6$alkoxyalkyl, $C_1$-$C_8$alkylaminoalkyl, substituted or unsubstituted $C_3$-$C_6$cycloalkyl, substituted or unsubstituted aryl, substituted or unsubstituted $C_2$-$C_8$heterocycloalkyl, substituted or unsubstituted heteroaryl, $C_1$-$C_4$alkyl(aryl), $C_1$-$C_4$alkyl(phenyl), $C_1$-$C_4$alkyl(heteroaryl), $C_1$-$C_4$alkyl($C_3$-$C_8$cycloalkyl), or $C_1$-$C_4$alkyl($C_2$-$C_8$heterocycloalkyl), or $C_1$-$C_8$alkylaminoalkyl;

R is H, or $C_1$-$C_6$alkyl; and pharmaceutically acceptable solvates or pharmaceutically acceptable salts thereof.

Suitable embodiments of such pyrimidine-based Btk inhibitor compounds are described in more detail in U.S. Pat. Nos. 8,088,781, 8,008,309, and 7,514,444 and related pending applications, the disclosures of which are expressly incorporated by reference herein.

In another embodiment, the mobilizing Btk inhibitor for use in the subject invention is selected from a compound of structural Formula II:

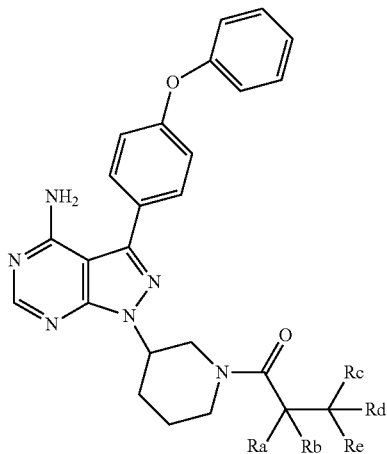

wherein:

Ra, Rb, Rc, Rd, and Re, are each independently selected from H, F, Cl, Br, I, —CN, —$SR_2$, —$OR_3$, $CO_2R_3$; or Ra, or Rb together with one of Rc, Rd and Re, and the carbon atoms to which they are attached form an epoxide; wherein Ra, Rb, Rc, Rd, and Re, cannot all be H;

$R_2$ is selected from H, methyl, ethyl, n-propyl, iso-propyl, n-butyl, iso-butyl, tert-butyl, a cysteinyl, a glutathionyl, $C_1$-$C_4$alkyl, a cysteinyl, or a glutathionyl;

$R_3$ is selected from H, $C_1$-$C_4$alkyl, phenyl, or benzyl; or a pharmaceutically acceptable salt thereof; and pharmaceutically acceptable solvates or pharmaceutically acceptable salts thereof.

Suitable embodiments of such pyrimidine-based Btk inhibitor compounds are described in more detail in U.S. Pat. No. 7,718,662 and related pending applications, the disclosures of which are expressly incorporated by reference herein.

In another embodiment, the mobilizing Btk inhibitor for use in the subject invention is selected from a compound of structural Formula III:

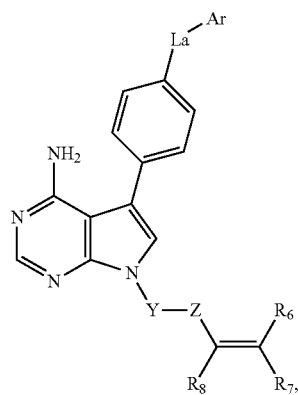

wherein:

La is O or S;

Ar is an unsubstituted phenyl;

Y is a 4-, 5-, 6-, or 7-membered cycloalkyl ring, or

Y is a 4-, 5-, 6-, or 7-membered monocyclic nitrogen containing heterocyclic ring;

Z is C(=O), OC(=O), NHC(=O), S(=O)$_x$, or NHS(=O)$_x$, where x is 2;

$R_8$ is H; $R_7$ is H, unsubstituted $C_1$-$C_4$ alkyl, $C_1$-$C_6$alkoxyalkyl, $C_1$-$C_8$alkylaminoalkyl, or $C_1$-$C_4$alkyl (phenyl); or $R_7$ and $R_8$ taken together form a bond;

$R_6$ is H, unsubstituted $C_1$-$C_4$ alkyl, $C_1$-$C_6$alkoxyalkyl, $C_1$-$C_8$alkylaminoalkyl, or $C_1$-$C_4$alkyl(phenyl); and pharmaceutically acceptable solvates or pharmaceutically acceptable salts thereof.

Suitable embodiments of such pyrimidine compounds are described in more detail in U.S. Pat. No. 7,960,396 and related pending applications. Additional Btk inhibitor compounds of interest include those described in U.S. Pat. No. 7,989,465, the disclosure of which is expressly incorporated by reference herein.

In the scope of the embodiments, the Btk inhibitors described herein include further forms of the compounds such as pharmaceutically acceptable salts, solvates (including hydrates), amorphous phases, partially crystalline and crystalline forms (including all polymorphs), prodrugs, metabolites, N-oxides, isotopically-labeled, epimers, pure epimers, epimer mixtures, enantiomers including but not limited to single enantiomers and enantiomeric diastereomers, meso compounds, stereoisomers, racemic mixtures and diasteroisomeric mixtures. Btk inhibitors described herein having one or more double bonds include cis/trans isomers, E/Z isomers and geometric isomers. Btk inhibitors described herein can be prepared as a pharmaceutically acceptable salts formed when an acidic proton present in the parent compound either is replaced by a metal ion, for example an alkali metal ion, an alkaline earth ion, or an aluminum ion; or coordinates with an organic base. In addition, the salt forms of the disclosed compounds can be prepared using salts of the starting materials or intermediates.

In some embodiments, a Btk inhibitor of the disclosure is present in a composition as a salt. In some embodiments, salts are obtained by reacting a compound of the disclosure with acids. In some other embodiments, pharmaceutically acceptable salts are obtained by reacting a compound of the disclosure with a base. In other embodiments, the compounds are used as free-acid or free-base form in the manufacture of the compositions described herein. The type of salts, include, but are not limited to: (1) acid addition salts, formed by reacting the free base form of the compound with a pharmaceutically acceptable: inorganic acid, such as, for example, hydrochloric acid, hydrobromic acid, sulfuric acid, phosphoric acid, metaphosphoric acid, and the like; or with an organic acid, such as, for example, acetic acid, propionic acid, hexanoic acid, cyclopentanepropionic acid, glycolic acid, pyruvic acid, lactic acid, malonic acid, succinic acid, malic acid, maleic acid, fumaric acid, trifluoroacetic acid, tartaric acid, citric acid, benzoic acid, 3-(4-hydroxybenzoyl)benzoic acid, cinnamic acid, mandelic acid, methanesulfonic acid, ethanesulfonic acid, 1,2-ethanedisulfonic acid, 2-hydroxyethanesulfonic acid, benzenesulfonic acid, toluenesulfonic acid, 2-naphthalenesulfonic acid, 4-methylbicyclo-[2.2.2]oct-2-ene-1-carboxylic acid, glucoheptonic acid, 4,4'-methylenebis-(3-hydroxy-2-ene-1-carboxylic acid), 3-phenylpropionic acid, trimethylacetic acid, tertiary butylacetic acid, lauryl sulfuric acid, gluconic acid, glutamic acid, hydroxynaphthoic acid, salicylic acid, stearic acid, muconic acid, butyric acid, phenylacetic acid, phenylbutyric acid, valproic acid, and the like; (2) salts formed when an acidic proton present in the parent compound is replaced by a metal ion, e.g., an alkali metal ion (e.g. lithium, sodium, potassium), an alkaline earth ion (e.g. magnesium, or calcium), or an aluminum ion. In some cases, the Btk inhibitor described herein are reacted with an organic base, such as, but not limited to, ethanolamine, diethanolamine, triethanolamine, tromethamine, N-methylglucamine, dicyclohexylamine, tris(hydroxymethyl)methylamine. In other cases, the compounds described herein form salts with amino acids such as, but not limited to, arginine, lysine, and the like. Acceptable inorganic bases used to form salts with compounds that include an acidic proton, include, but are not limited to, aluminum hydroxide, calcium hydroxide, potassium hydroxide, sodium carbonate, sodium hydroxide, and the like.

When the Btk inhibitors described herein include one or more chiral centers, the stereochemistry of such chiral centers can independently be in the R or S configuration, or a mixture of the two. The chiral centers can be further designated as R or S or R, S or d, D, l, L or d, l, D, L. Correspondingly, the Btk inhibitors of the invention, if they can be present in optically active form, can actually be present in the form of a racemic mixture of enantiomers, or in the form of either of the separate enantiomers in substantially isolated and purified form, or as a mixture comprising any relative proportions of the enantiomers.

When the Btk inhibitors described herein contain two or more chiral centers then diastereomers are possible. Such diastereomers may be present as pure diastereomeric enantiomers, pure racemic mixtures of diastereomeric enantiomers, mixtures of diastereomers which may be racemic or may have optical activity in their own right due to complex permutations of enantiomeric diastereomers in the balance of the mixtures.

When the Btk inhibitors of the invention can be present in geometrically isomeric forms, then they can actually be present in the form of a mixture of geometric isomers comprising any relative proportions of the isomers, or in some cases in the form of either of the separate geometric isomers in substantially isolated and purified form.

When the Btk inhibitors described herein include one or more isolated or linearly conjugated double bonds, the geometry around such double bonds can be independently a cis/trans, E/Z mixture or an E or Z geometric isomer thereof.

In some embodiments, the Btk inhibitors described herein include solvent addition forms or crystal forms thereof, particularly solvates or polymorphs. Solvates contain either stoichiometric or non-stoichiometric amounts of a solvent, and may be formed during the process of crystallization with pharmaceutically acceptable solvents such as water, ethanol, and the like. Hydrates are formed when the solvent is water, or alcoholates are formed when the solvent is alcohol.

As noted above, in some embodiments the Btk inhibitors described herein possess one or more stereocenters and each center exists independently in either the R or S configuration. The Btk inhibitors presented herein include all diastereomeric, enantiomeric, and epimeric forms as well as the appropriate mixtures thereof.

In some embodiments, sites on the Btk inhibitors disclosed herein are susceptible to various metabolic reactions. Therefore incorporation of appropriate substituents at the places of metabolic reactions will reduce, minimize or eliminate the metabolic pathways. In specific embodiments, the appropriate substituent to decrease or eliminate the susceptibility of the aromatic ring to metabolic reactions is, by way of example only, a halogen, deuterium or an alkyl group.

In some embodiments, the Btk inhibitors described herein are isotopically-labeled, which are identical to those recited in the various formulae and structures presented herein, but for the fact that one or more atoms are replaced by an atom having an atomic mass or mass number different from the atomic mass or mass number usually found in nature. In some embodiments, one or more hydrogen atoms are replaced with deuterium. In some embodiments, metabolic sites on the compounds described herein are deuterated. In some embodiments, substitution with deuterium affords certain therapeutic advantages resulting from greater metabolic stability, such as, for example, increased in vivo half-life or reduced dosage requirements. Throughout the specification, groups and substituents thereof can be chosen by one skilled in the field to provide stable moieties and compounds.

Inhibitors of Btk kinase activity preferably inhibit Btk activity with an $IC_{50}$ of less than or equal to 10 micromolar, less than or equal to 1 micromolar, less than or equal to 500 nanomolar, less than or equal to 100 nanomolar, or less than or equal to 10 nanomolar in an ADP-GLO™, bioluminescent, homogeneous assay or in a HTRF® (Homogeneous Time-Resolved Fluorescence) assay.

Inhibitors of Bruton's tyrosine kinase activity preferably inhibit phosphorylation of Y551 of Btk with an $IC_{50}$ of less than or equal to 10 micromolar, less than or equal to 1 micromolar, less than or equal to 500 nanomolar, less than or equal to 112 nanomolar, less than or equal to 100 nanomolar, or less than or equal to 10 nanomolar.

Inhibitors of Bruton's tyrosine kinase activity preferably inhibit phosphorylation of Y223 of Btk with an $IC_{50}$ of less than or equal to 10 micromolar, less than or equal to 1 micromolar, less than or equal to 500 nanomolar, less than or equal to 112 nanomolar, less than or equal to 100 nanomolar, or less than or equal to 10 nanomolar. Inhibitors of Bruton's tyrosine kinase activity may inhibit phosphorylation of downstream PLCγ2 with an $IC_{50}$ of less than or equal to 10 micromolar, less than or equal to 1 micromolar, less than or equal to 500 nanomolar, less than or equal to 100 nanomolar, or less than or equal to 10 nanomolar in, e.g., an IgM phospho-PLCg2 assay.

The compounds described herein, and other related compounds having different substituents can be synthesized using techniques and materials known to those of skill in the art, such as described, for example, in March, ADVANCED ORGANIC CHEMISTRY 4th Ed., (Wiley 1992); Carey and Sundberg, ADVANCED ORGANIC CHEMISTRY 4th Ed., Vols. A and B (Plenum 2000, 2001), and Green and Wuts, PROTECTIVE GROUPS IN ORGANIC SYNTHESIS 3rd Ed., (Wiley 1999) (all of which are incorporated by reference in their entirety). General methods for the preparation of the compounds as disclosed herein may be derived from known reactions in the field, and the reactions may be modified by the use of appropriate reagents and conditions, as would be recognized by the skilled person, for the introduction of the various moieties found in the formulae as provided herein. Appropriate synthesis methods for the subject pyrimidine compounds are described in more detail in U.S. Pat. Nos. 8,088,781, 8,008,309, 7,718,662, 7,514,444 and 7,960,396.

Also disclosed herein are pharmaceutical compositions. The pharmaceutical compositions will generally comprise a pharmaceutically acceptable carrier and a pharmacologically effective amount of the compounds, or mixture of thereof, or suitable salts thereof. The pharmaceutical composition may be formulated as powders, granules, solutions, suspensions, aerosols, solids, pills, tablets, capsules, gels, topical cremes, suppositories, transdermal patches, and other formulations known in the art.

As used herein, "pharmaceutically acceptable carrier" comprises any of standard pharmaceutically accepted carriers known to those of ordinary skill in the art in formulating pharmaceutical compositions. Thus, the compounds, by themselves, such as being present as pharmaceutically acceptable salts, or as conjugates, may be prepared as formulations in pharmaceutically acceptable diluents; for example, saline, phosphate buffer saline (PBS), aqueous ethanol, or solutions of glucose, mannitol, dextran, propylene glycol, oils (e.g., vegetable oils, animal oils, synthetic oils, etc.), microcrystalline cellulose, carboxymethyl cellulose, hydroxylpropyl methyl cellulose, magnesium stearate, calcium phosphate, gelatin, polysorbate 80 or the like, or as solid formulations in appropriate excipients.

The pharmaceutical compositions will often further comprise one or more buffers (e.g., neutral buffered saline or phosphate buffered saline), carbohydrates (e.g., glucose, mannose, sucrose or dextrans), mannitol, proteins, polypeptides or amino acids such as glycine, antioxidants (e.g., ascorbic acid, sodium metabisulfite, butylated hydroxytoluene, butylated hydroxyanisole, etc.), bacteriostats, chelating agents such as EDTA or glutathione, solutes that render the formulation isotonic, hypotonic or weakly hypertonic with the blood of a recipient, suspending agents, thickening agents, preservatives, flavoring agents, sweetening agents, and coloring compounds as appropriate.

While any suitable carrier known to those of ordinary skill in the art may be employed in the compositions, the type of carrier will typically vary depending on the mode of administration. The therapeutic compositions may be formulated for any appropriate manner of administration, including for example, oral, nasal, mucosal, rectal, vaginal, topical, intravenous, intraperitoneal, intradermal, subcutaneous, and intramuscular administration.

For parenteral administration, the compositions can be administered as injectable dosages of a solution or suspension of the substance in a physiologically acceptable diluent with a pharmaceutical carrier that can be a sterile liquid such as sterile pyrogen free water, oils, saline, glycerol, polyethylene glycol or ethanol. Additionally, auxiliary substances, such as wetting or emulsifying agents, surfactants, pH buffering substances and the like can be present in compositions. Other components of pharmaceutical compositions are those of petroleum, animal, vegetable, or synthetic origin, for example, non-aqueous solutions of peanut oil, soybean oil, corn oil, cottonseed oil, ethyl oleate, and isopropyl myristate.

Sterile injectable solutions can be prepared by incorporating the mobilizing Btk inhibitor in the required amount in an appropriate solvent with one or a combination of ingredients enumerated above, as required, followed by filtered sterilization. Generally, dispersions are prepared by incorporating the active compound into a sterile vehicle that contains a basic dispersion medium and the required other ingredients from those enumerated above. In the case of sterile powders for the preparation of sterile injectable solutions, the preferred methods of preparation are vacuum drying and freeze-drying which yields a powder of the active ingredient plus any additional desired ingredient from a previously sterile-filtered solution thereof. In accordance with an alternative aspect of the invention, an agent of the invention as described above may be formulated with one or more additional compounds that enhance the solubility of these agents. The invention also extends to such derivatives of such agents of the invention.

The pharmaceutical compositions described herein may be presented in unit-dose or multi-dose containers, such as sealed ampoules or vials. Such containers are typically sealed in such a way to preserve the sterility and stability of the formulation until use. In general, formulations may be stored as suspensions, solutions or emulsions in oily or aqueous vehicles, as indicated above. Alternatively, a pharmaceutical composition may be stored in a freeze-dried condition requiring only the addition of a sterile liquid carrier immediately prior to use. In one embodiment, a pharmaceutical composition is provided comprising expanded hematopoietic progenitor cells cryopreserved in a suitable cryopreservation medium, which can then be thawed and resuspended as needed for administration to a patient.

The pharmaceutical compositions described herein can also contain the mobilizing Btk inhibitor in a form suitable for oral use, for example, as tablets, troches, lozenges, aqueous or oily suspensions, dispersible powders or granules, emulsions, hard or soft capsules, or syrups or elixirs. Compositions intended for oral use can be prepared according to any method known to the art for the manufacture of pharmaceutical compositions, and such compositions can contain one or more agents selected from, by way of non-limiting example, sweetening agents, flavoring agents, coloring agents and preserving agents in order to provide pharmaceutically elegant and palatable preparations.

Formulations suitable for oral administration can be presented as discrete units such as capsules, cachets or tablets each containing a predetermined amount of the active ingredient; as a powder or granules; as a solution or a suspension in an aqueous liquid or a non-aqueous liquid; or as an oil-in-water liquid emulsion or a water-in-oil liquid emulsion.

Composition preparations which can be used orally include tablets, push-fit capsules made of gelatin, as well as soft, sealed capsules made of gelatin and a plasticizer, such as glycerol or sorbitol. Tablets can be made by compression or molding, optionally with one or more accessory ingredients. Compressed tablets can be prepared by compressing in a suitable machine the active ingredient in a free-flowing form such as a powder or granules, optionally mixed with binders (e.g., povidone, gelatin, hydroxypropylmethyl cellulose), inert diluents, preservative, disintegrant (e.g., sodium starch glycolate, cross-linked povidone, cross-linked sodium carboxymethyl cellulose) or lubricating, surface active or dispersing agents. Molded tablets can be made by molding in a suitable machine a mixture of the powdered compound moistened with an inert liquid diluent. The tablets can optionally be coated or scored and can be formulated so as to provide slow or controlled release of the active ingredient therein. Tablets can optionally be provided with an enteric coating, to provide release in parts of the gut other than the stomach. All formulations for oral administration should be in dosages suitable for such administration. The push-fit capsules can contain the active ingredients in admixture with filler such as lactose, binders such as starches, and/or lubricants such as talc or magnesium stearate and, optionally, stabilizers. In soft capsules, the active compounds can be dissolved or suspended in suitable liquids, such as fatty oils, liquid paraffin, or liquid polyethylene glycols. In addition, stabilizers can be added. Dragee cores are provided with suitable coatings. For this purpose, concentrated sugar solutions can be used, which can optionally contain gum arabic, talc, polyvinyl pyrrolidone, carbopol gel, polyethylene glycol, and/or titanium dioxide, lacquer solutions, and suitable organic solvents or solvent mixtures. Dyestuffs or pigments can be added to the tablets or Dragee coatings for identification or to characterize different combinations of active compound doses.

It should be understood that in addition to the ingredients particularly mentioned above, the compounds and compositions described herein can include other agents conventional in the art having regard to the type of formulation in question, for example those suitable for oral administration can include flavoring agents.

In some embodiments, one or more mobilizing Btk inhibitor may be formulated in pharmaceutical compositions with additional active ingredients, or administered in methods of treatment in conjunction with treatment with one or more additional medications, such as another agent as described herein that also increases mobilization of stem cells, for example, or one or more agents selected from the group consisting of: recombinant-methionyl human. G-CSF (NEUPOGEN®, Filgastim; Amgen), GM-CSF (LEUKINE®, Sargramostim; Immunex), erythropoietin (rhEPO, EPOGEN®; Amgen), thrombopoietin (rhTPO; Genentech), interleukin-11 (rhlL-11, NEUMEGA®; American Home Products), Flt3 ligand (Mobista; Immunex), multilineage hematopoietic factor (MARSTEM™; Maret Pharm.), myelopoietin (Leridistem; Searle), IL-3, myeloid progenitor inhibitory factor-1 (Mirostipen; Human Genome Sciences), stem cell factor (rhSCF, STEMGEN®; Amgen), and plerixafor (Mozobil®; Genzyme-Sanofi).

The amount administered to the host will vary depending upon what is being administered, the purpose of the administration, such as prophylaxis or therapy, the state of the host, the manner of administration, the number of administrations, interval between administrations, and the like. These can be determined empirically by those skilled in the art and may be adjusted for the extent of the therapeutic response. Factors to consider in determining an appropriate dose include, but is not limited to, size and weight of the subject, the age and sex of the subject, the severity of the symptom, the stage of the disease, method of delivery of the agent, half-life of the agents, and efficacy of the agents. Stage of the disease to consider includes whether the disease is acute or chronic, relapsing or remitting phase, and the progressiveness of the disease.

Determining the dosages and times of administration for a therapeutically effective amount are well within the skill of the ordinary person in the art. For example, an initial effective dose can be estimated from cell culture or other in vitro assays. A dose can then be formulated in animal models to generate a circulating concentration or tissue concentration, including that of the $IC_{50}$ as determined by the cell culture assays.

In addition, toxicity and therapeutic efficacy are generally determined by cell culture assays and/or using experimental animals, typically by determining a $LD_{50}$ (lethal dose to 50% of the test population) and $ED_{50}$ (therapeutically effectiveness in 50% of the test population). Guidance is found in standard reference works, for example, Goodman & Gilman's The Pharmacological Basis of Therapeutics, $10^{th}$ Ed. (Hardman, J. G. et al., eds.) McGraw-Hill, New York, N.Y. (2001).

For the purposes of this invention, the methods of administration are chosen depending on the condition being treated, the form of the subject mobilizing Btk inhibitor(s), and the pharmaceutical composition. Administration of the therapeutic compounds can be done in a variety of ways, including, but not limited to, orally subcutaneously, intravenously, intraperitoneally, intramuscularly, and possibly direct injection to specified organs such as e.g., spleen or bone marrow, although systemic and oral administration are preferred. Administration of the pharmaceutical compositions may be through a single route or concurrently by several routes.

The compositions may be administered once per day, a few or several times per day, or even multiple times per day, depending upon, among other things, the indication being treated and the judgment of the prescribing physician.

As disclosed above, disclosed herein are mobilizing Btk inhibitors and pharmaceutical compositions comprising the same. The mobilizing Btk inhibitors and pharmaceutical compositions can be administered to a subject to mobilize the subject's hematopoietic stem and progenitor cells into the peripheral blood of the subject. Accordingly, a mobilizing Btk inhibitor may be administered to a subject in need thereof, e.g., a patient having impaired hematopoiesis and/or deficient in white blood cells such as myeloid and lymphoid cells.

Impaired Hematopoiesis

A variety of diseases, in particular cancers and hyperproliferative disorders, require treatment with agents that are preferentially cytotoxic to dividing cells. These therapies typically include high doses of irradiation and/or chemotherapeutic agents. While necessary to kill off the cancer cells, a significant side effect of these approaches is the pathological impact of such treatments on rapidly dividing normal cells, such as hair follicles, mucosal cells and the hematopoietic cells, including primitive hematopoietic progenitor cells and stem cells. This indiscriminate destruction of hematopoietic stem cells and progenitor/precursor cells leads to reduced mature blood cell counts, such as lymphocytes, neutrophils and platelets, eventually resulting in a loss of immune system function in these patients and a substantially increased risk of morbidity and mortality from opportunistic infections. Leukopenia resulting from chemotherapy or irradiation therapy may occur within a few days following cytotoxic treatments, although the patient can be vulnerable to infection for up to one month until the white blood cell counts recover to within a normal range. If the reduced leukocyte count (leukopenia), neutrophil count (neutropenia), granulocyte count (granulocytopenia) and/or platelet count (thrombocytopenia) become sufficiently serious, the therapy must be interrupted to allow for recovery of the white blood cells, which may in turn result in the survival of cancer cells, an increase drug resistance in the cancer cells, and may actually result in a relapse of the cancer.

The methods of mobilizing progenitor cells and/or providing hematopoietic cells to a patient disclosed herein may be used for the treatment of such impaired hematopoiesis. A treatment modality that enhances the stem and/or progenitor cells in blood is helpful in treatments to ameliorate the effects of conditions that adversely affect the bone marrow, such as chemotherapy or irradiation (intentional or accidental) that results in leukopenia, including neutropenia, and thrombocytopenia. The mobilizing Btk inhibitors disclosed herein may enhance the success of bone marrow transplantation, and may combat infections in the patient undergoing such therapies. In this context the compounds are also be used to mobilize and harvest hematopoietic stem cells or progenitor cells via apheresis and the harvested cells are used in treatments requiring stem cell transplantations. Furthermore, the Btk inhibitors can be used both in vivo to promote mobilization of hematopoietic stem cells or progenitor cells from the bone marrow to the peripheral blood or can be used for ex vivo studies, whereby a patient's own stem cells are removed and expanded in culture for autologous transplants. Also contemplated by the present invention are in vitro screens, whereby candidate or test compounds can be measured for their effects on mobilization before being administered in vivo.

In some embodiments, the disorder relates to impairment of hematopoiesis caused by disease or myeloablative treatments. As used herein, "treatment" refers to therapeutic or prophylactic treatment. Treatment encompasses administration of a Btk inhibitor capable of mobilizing hematopoietic stem and progenitor cells to the peripheral blood of a first subject, and optionally harvesting said mobilized progenitor cells and introducing them into a compatible subject. In one embodiment, the obtained progenitor cells are cultured ex vivo prior to re-introduction into the original subject. In one embodiment, the obtained progenitor cells are cultured ex vivo prior to introduction into a second subject. In one embodiment, the methods comprise administration of the obtained, and optionally cultured, cells in an appropriate form prior to the onset of disease symptoms and/or after clinical manifestations, or other manifestations of the disease or condition to reduce disease severity, halt disease progression, or eliminate the disease.

"Prophylactic" or "therapeutic" treatment refers to administration to the subject of one or more of the Btk inhibitor compositions. If it is administered prior to clinical manifestation of the impaired hematopoiesis (e.g., leukopenia or neutropenia) then the treatment is prophylactic, i.e., it protects the host against developing the unwanted condition, whereas if administered after manifestation of impaired hematopoiesis, the treatment is therapeutic (i.e., it is intended to improve hematopoiesis and/or increase white blood cell count). "Subject" refers to a mammal, preferably a human, in need of treatment for a condition, disorder or disease.

For example, myelosuppressive chemotherapy regimens with cytotoxic agents such as doxorubicin, paclitaxel, cisplatin, carboplatin, etoposide, ifosfamide, daunorubicin, cytosine arabinoside, thioguanine, and the like typically induce a transient but profound myelosuppression in patients, at about seven to fourteen days after chemotherapy. This maybe followed by rapid reappearance of leukocytes in the peripheral blood and a "rebound" increase of the circulating leukocytes above baseline levels. As the leukocyte count rises, hematopoietic progenitor cells also begin to appear in the peripheral blood and rapidly increase. Protocols involving dose intensification (i.e., to increase the log-kill of the respective tumor therapy) or schedule compression may exacerbate the degree and duration of myelosuppression associated with the chemotherapy and/or radiation therapy. For instance, in the adjuvant setting, repeated cycles of doxorubicin-based treatment have been shown to produce cumulative and long-lasting damage in the bone marrow progenitor cell populations (Lorhrman et al., (1978) Br. J. Haematol. 40:369).

The effect of this short-term hematopoietic cell damage resulting from chemotherapy has been addressed to some extent by the concurrent use of G-CSF (Neupogen®), which is used to accelerate the regeneration of neutrophils (Le Chevalier (1994) Eur. J. Cancer 30A:410). This approach has met with limitations, however, as it may be accompanied by progressive thrombocytopenia and cumulative bone marrow damage as reflected by a reduction in the quality of mobilized progenitor cells over successive cycles of treatment. Because of the current interest in chemotherapy dose intensification as a means of improving tumor response rates and patient survival, the necessity for alternative therapies to either improve or replace current treatments to rescue the myelosuppressive effects of chemotherapy and/or radiation therapy has escalated, and is currently one of the major rate limiting factors for tumor therapy dose escalations.

In the present invention, treatments using the mobilizing Btk inhibitors described may be provided to patients suffering from a cancerous condition or hyperproliferative disease, whereby the treatment of the disease with chemotherapy or irradiation therapy results in a decrease in bone marrow cellularity, thus making the patient more prone to acquiring infectious agents or diseases. Thus, administration of the mobilizing Btk inhibitors of the present invention subsequent to the chemotherapy and/or radiation exposure allows for the mobilization of hematopoietic stem and/or progenitor cells from the bone marrow to the peripheral blood. As used herein "subsequent" administration may be within 1-24 hours, preferably within 12 to 24 or 24 to 36 or 48 hours, preferably within one to 30 days, more preferably within one to 14 or 21 days, more preferably within three or five to ten or fourteen days after the chemotherapy and/or radiation exposure. Improving hematopoiesis may advantageously allow for the use of accelerated doses of chemotherapy or irradiation therapy.

Additionally, transplantation of hematopoietic stem and progenitor cells harvested from a subject may provide a more rapid and sustained hematopoietic recovery, e.g, after the administration of high-dose chemotherapy or radiation therapy in patients with hematological malignancies and solid tumours. This has become the preferred source of hematopoietic stem cells for autologous transplantation because of the shorter time to engraftment and the lack of a need for surgical procedures such as are necessary for bone marrow harvesting (Demirer et al. (1996) Stem Cells 14:106-116; Pettengel et al., (1992) Blood 82:2239-2248). Moreover, this approach has been successfully used in the allogeneic setting as well as in the syngeneic setting, including in the context of more differentiated hematopoietic progenitor cells, e.g., myeloid progenitor cells. See, e.g., U.S. Pat. Nos. 8,252,587 and 8,383,095, the disclosures of which are expressly incorporated by reference herein.

It is possible to expand hematopoietic stem and progenitor cells in stroma-containing or nonstromal systems. Expansion systems have reportedly shown increases in CFU_GM of more than 100-fold. Enrichment of CD34+ cells may be required before expansion in nonstromal culture but may not be necessary in stroma-containing systems. Early results of clinical trials are encouraging and have been taken to demonstrate that the engraftment potential of the expanded hematopoietic cells is not compromised by culture. Other possible applications of stem cell expansion include purging of tumor cells; production of immune-competent cells, such as dendritic cells and NK cells, and gene therapy.

Enrichment of Common Lymphoid Progenitors

Hematopoietic stem cells and progenitors may be obtained from a subject according to the methods described herein, and enriched for and/or further differentiated into progenitors of different lineages according to well-known methods. For example, common lymphoid progenitor cells, which give rise to B cells, T cells, and Natural Killer Cells, common myeloid progenitor cells which give rise to monocytes, granulocytes, megakaryocytes, and erythrocytes may be enriched by sorting according to the expression levels of certain growth factor receptors. See, e.g., U.S. Pat. Nos. 7,979,057; 7,235,623; 6,908,763; and 5,989,660, the disclosures of which are expressly incorporated by reference herein.

For example, common lymphoid progenitors (CLPs) express low levels of c-kit (CD117) on their cell surface. Antibodies that specifically bind c-kit in humans, mice, rats, etc. are known in the art. Alternatively, the c-kit ligand, steel factor (Slf) may be used to identify cells expressing c-kit. The CLP cells express high levels of the IL-7 receptor alpha chain (CDw127). Antibodies that bind to human or to mouse CDw127 are known in the art. Alternatively, the cells are identified by binding of the ligand to the receptor, IL-7.

Murine CLPs express low levels of Sca-1 (Ly-6E and Ly-6A, see van de Rijn (1989) *Proc Natl Acad Sci* 86:4634-4638). Antibodies specific for Sca-1 are known in the art. The expression of high levels of Sca-1 on murine hematopoietic stem cells has been previously described (Spangrude et al. (1988) *J Immunol* 141:3697-3707). A candidate human counterpart for Sca-1 is described in Hill et al. (1996) *Exp Hematol* 24:936-943, as high-level expression of a novel epitope of CD59 identifies a subset of CD34+ bone marrow cells that are highly enriched for pluripotent stem cells.

The CLP subset also has the phenotype of lacking expression of lineage specific markers, exemplified by B220, CD4, CD8, CD3, Gr-1 and Mac-1. For staining purposes a cocktail of binding reagents, herein designated "lin", may be used. The lin panel will comprise binding reagents, e.g. antibodies and functional binding fragments thereof, ligands, peptidomimetics, etc., that recognize two or more of the lineage markers. A lin panel will generally include at least one marker expressed on mature B cells, on mature T cells, on mature granulocytes and on mature macrophages. Markers suitable for use in a lineage panel are typically expressed on these mature cells, but are not present on multiple lineages, or on stem and progenitor cells. The subject cells are characterized as lacking expression of Thy-1, a marker that is characteristic of hematopoietic stem cells. The phenotype of the CLP may be further characterized as Mel-14$^-$, CD43l$^o$, HSA$^{lo}$, CD45$^+$ and common cytokine receptor $\gamma$ chain Enrichment of Myeloid Progenitors Myeloid progenitors may be subdivided into three distinct subsets: a common myeloid progenitor cell (CMP) which is characterized by progenitor cell activity for myeloid lineages, but lacking the potential to differentiate into lymphoid lineages; a granulocyte monocyte (GMP) committed progenitor cell; and an erythroid/megakaryocyte (MEP) committed progenitor cell. The CMP gives rise to the other two subsets.

The CMP population is useful in transplantation to provide a recipient with myeloid cells, including megakaryocytes, platelets and erythroid cells, in addition to monocytes and granulocytes; for drug screening; experimental models of hematopoietic differentiation and interaction; screening in vitro assays to define growth and differentiation factors, and to characterize genes involved in myeloid development and regulation; and the like. The native cells may be used for these purposes, or they may be genetically modified to provide altered capabilities.

Each of these progenitor subsets may be are separated from a complex mixture of cells by using reagents that specifically recognize markers on the cell surface. In both human and mouse cells, all three of the myeloid lineage progenitors stain negatively for the markers Thy-1 (CD90), IL-7R.alpha. (CD127); and with a panel of lineage markers, which lineage markers may include CD2; CD3; CD4; CD7; CD8; CD10; CD11b; CD14; CD19; CD20; CD56; and glycophorin A (GPA) in humans and CD2; CD3; CD4; CD8; CD19; IgM; Ter110; Gr-1 in mice. With the exception of the mouse MEP subset, all of the progenitor cells are CD34 positive. In the mouse all of the progenitor subsets may be further characterized as Sca-1 negative, (Ly-6E and Ly-6A), and c-kit high. In the human, all three of the subsets are CD38$^+$.

Among the progenitor subsets, that is, the population of cells defined as Lin$^-$ IL-7R$^-$ Thy-1$^-$, the population can be divided into subsets for the CMP, GMP and MEP cells. In humans, the markers IL-3R$\alpha$ (CDw127) and CD45RA are sufficient for separating the three subsets, where the CMP is IL-3R$\alpha^{lo}$ CD45RA$^-$; the GMP is IL-3R$\alpha^{lo}$ CD45R$\alpha^+$; and the MEP is IL-3R$\alpha^-$ CD45RA$^-$. In the mouse, the CD34 and Fc$\gamma$ receptor (Fc$\gamma$R) are useful in making these distinctions. The CMP is characterized as Fc$\gamma$R$^{lo}$ CD34$^+$ population; the GMP is Fc$\gamma$R$^{hi}$ CD34$^+$; and the MEP subset is Fc$\gamma$R$^{lo}$ CD34$^-$.

In the presence of steel factor (SLF), flt-3 ligand (FL), interleukin (IL)-3, IL-11, GM-CSF, thrombopoietin (Tpo) and erythropoietin (Epo), the CMP cells give rise to various types of myeloerythroid colonies, including CFU-GEM-Meg, burst-forming unit-erythroid (BFU-E), CFU-megakaryocytes (CFU-Meg), CFU-granulocyte/macrophage (CFU-GM), CFU-granulocyte (CFU-G) and CFU-macrophage (CFU-M).

The GMP subset generates CFU-M, CFU-G, or CFU-GM colonies containing macrophages and/or granulocytes in response to the above growth factors. In contrast, the MEP subset gives rise to CFU-Meg, BFU-E, or CFU-MEP colonies containing only megakaryocytes and/or erythrocytes in response to IL-3, GM-CSF, Tpo and Epo, but do not form colonies in the absence of Tpo and Epo. All three myeloid progenitor populations do not require "early-acting cytokines" such as SLF, FL and IL-11 to initiate colony formation.

All of these progenitors are capable of rapid differentiation activity in vivo. CMP cells give rise to Gr-1+/Mac-1+ myelomonocytic cells and megakaryocytic colonies, as well as TER119+ erythroid cells in spleen and bone marrow. The GMP progenitor population gives rise to Gr-1+/Mac-1+ cells; and the MEP progenitor population to megakaryocytes and erythroid cells.

The subject subsets may be separated from a complex mixture of cells by techniques that enrich for cells having the above-described characteristics for the subset of interest. An appropriate solution may be used for dispersion or suspension. Such solution will generally be a balanced salt solution, e.g. normal saline, PBS, Hank's balanced salt solution, etc., conveniently supplemented with fetal calf serum or other naturally occurring factors, in conjunction with an acceptable buffer at low concentration, generally from 5-25 mM. Convenient buffers include HEPES, phosphate buffers, lactate buffers, etc.

Separation of the subject cell populations may be attained by use of affinity separation to provide a substantially pure population. Techniques for affinity separation may include magnetic separation, using antibody-coated magnetic beads, affinity chromatography, cytotoxic agents joined to a monoclonal antibody or used in conjunction with a monoclonal antibody, e.g. complement and cytotoxins, and "panning" with antibody attached to a solid matrix, e.g. plate, or other convenient technique. Techniques providing accurate separation include fluorescence activated cell sorters, which can have varying degrees of sophistication, such as multiple color channels, low angle and obtuse light scattering detecting channels, impedance channels, etc. The cells may be selected against dead cells by employing dyes associated with dead cells (e.g. propidium iodide). Any technique may be employed which is not unduly detrimental to the viability of the selected cells.

The affinity reagents may be specific receptors or ligands for the cell surface molecules indicated above. In addition to antibody reagents, peptide-MHC antigen and T cell receptor pairs may be used; peptide ligands and receptor; effector and receptor molecules, and the like. Antibodies and T cell receptors may be monoclonal or polyclonal, and may be produced by transgenic animals, immunized animals, immortalized human or animal B-cells, cells transfected with DNA vectors encoding the antibody or T cell receptor, etc. The details of the preparation of antibodies and their suitability for use as specific binding members are well-known to those skilled in the art.

Of particular interest is the use of antibodies as affinity reagents. Conveniently, these antibodies are conjugated with a label for use in separation. Labels include magnetic beads, which allow for direct separation, biotin, which can be removed with avidin or streptavidin bound to a support, fluorochromes, which can be used with a fluorescence activated cell sorter, or the like, to allow for ease of separation of the particular cell type. Fluorochromes that find use include phycobiliproteins, e.g. phycoerythrin and allophycocyanins, fluorescein and Texas red. Frequently each antibody is labeled with a different fluorochrome, to permit independent sorting for each marker.

The antibodies are added to a suspension of cells, and incubated for a period of time sufficient to bind the available cell surface antigens. The incubation will usually be at least about 5 minutes and usually less than about 30 minutes. It is desirable to have a sufficient concentration of antibodies in the reaction mixture, such that the efficiency of the separation is not limited by lack of antibody. The appropriate concentration is determined by titration. The medium in which the cells are separated will be any medium which maintains the viability of the cells. A preferred medium is phosphate buffered saline containing from 0.1 to 0.5% BSA. Various media are commercially available and may be used according to the nature of the cells, including Dulbecco's Modified Eagle Medium (dMEM), Hank's Basic Salt Solution (HBSS), Dulbecco's phosphate buffered saline (dPBS), RPMI, Iscove's medium, PBS with 5 mM EDTA, etc., frequently supplemented with fetal calf serum, BSA, HSA, etc.

The labeled cells are then separated as to the expression of cell surface markers as previously described. The separated cells may be collected in any appropriate medium that maintains the viability of the cells, usually having a cushion of serum at the bottom of the collection tube. Various media are commercially available and may be used according to the nature of the cells, including dMEM, HBSS, dPBS, RPMI, Iscove's medium, etc., frequently supplemented with fetal calf serum.

The culture may contain growth factors to which the cells are responsive. Growth factors, as defined herein, are molecules capable of promoting survival, growth and/or differentiation of cells, either in culture or in the intact tissue, through specific effects on a transmembrane receptor. Growth factors include polypeptides and non-polypeptide factors. Specific growth factors that may be used in culturing the subject cells include steel factor (c-kit ligand), Flk-2 ligand, IL-11, IL-3, GM-CSF, erythropoietin and thrombopoietin. The specific culture conditions are chosen to achieve a particular purpose, i.e. differentiation into erythroid of megakaryocyte populations, maintenance of progenitor cell activity, etc.

In addition to, or instead of growth factors, the subject cells may be grown in a co-culture with stromal or feeder layer cells. Stromal cells suitable for use in the growth of hematopoietic cells are known in the art. These include bone marrow stroma as used in "Whitlock-Witte" (Whitlock et al. [1985] Annu Rev Immunol 3:213-235) or "Dexter" culture conditions (Dexter et al. J Exp Med 145:1612-1616); and heterogeneous thymic stromal cells (Small and Weissman [1996] Scand J Immunol 44:115-121).

The subject cultured cells may be used in a wide variety of ways. The nutrient medium, which is a conditioned medium, may be isolated at various stages and the components analyzed. Separation can be achieved with HPLC, reversed phase-HPLC, gel electrophoresis, isoelectric focusing, dialysis, or other non-degradative techniques, which allow for separation by molecular weight, molecular volume, charge, combinations thereof, or the like. One or more of these techniques may be combined to enrich further for specific fractions.

EXAMPLES

Example 1

Inhibition of HSC Migration to SDF-1 In Vitro

Materials and Methods

Human CD34+ hematopoietic progenitor cells were isolated from G-CSF mobilized peripheral blood and incubated with varying concentrations (0.1 µM, 1.0 µM and 10 µM) of the pyrimidine-based BTK inhibitor 1-[(3R)-3-[4-amino-3-(4-phenoxyphenyl)pyrazolo[3,4-d]pyrimidin-1-yl]piperidin-1-yl]prop-2-en-1-one for one hour at 37° C., 5% CO2 in serum free media (0.5% bovine serum albumin in RPMI media). Cells were then transferred to the upper chamber of a Transwell migration plate (5.0 um pore size, Costar Inc.). The lower chamber contained only serum-free media with 100 ng/ml SDF-1. Cells were incubated for five hours at 37° C., 5% CO2 to allow for cell migration from the upper chamber to the lower chamber. Cells that migrated into the lower chamber were counted using a hemocytometer.

Results

As shown in FIG. 1, inhibition of stem cell migration was seen at all tested concentrations of the Btk inhibitor. Notably, the BTK inhibitor showed activity at a 500-fold lower concentration than reported for similar assays with plerixafor (50 µM).

Example 2

Murine CFU and LTR Assays

Materials and Methods

Mice

All strains of mice (C57Bl/6, Congenic C57Bl/6 [CD45.2+], B6.BoyJ [CD45.1+], and NOD/SCID) can be purchased from Jackson ImmunoResearch Laboratories.

Cells

Low-density mononuclear cells (LDMNC) are purified from mouse and human blood by density cut procedures using murine lympholyte and Ficoll Hypaque (Amersham Biosciences), respectively. Human CD34+ cells are isolated first into a LDMNC fraction and then purified by positive selection with a Magnetic Affinity Cell Separation CD34+ isolation kit (Miltenyi Biotec).

Colony Forming Cell Assays

Mice are assayed for CFU-GM, BFU-E, and CFUGEMM. Cells are cultured in Methocult GF+ media (StemCell Technologies, Vancouver) consisting of 1% methylcellulose, 30% FBS, 1% BSA, 50 ng/mL stem cell factor, 20 ng/mL granulocyte-macrophage colony-stimulating factor, 20 ng/mL IL-3, 20 ng/mL IL-6, 20 ng/mL granulocyte colony-stimulating factor, and 3 units/mL erythropoietin. Colonies are scored after seven days incubation in a humidified atmosphere with 5% CO2 and lowered (5%) O2. Colonies are scored as described in "Hematopoiesis: A Practical Approach" (1993) Oxford Press, pp 75-106.

Murine Long-Term Repopulation (LTR) Assay

The mouse LTR cell assay detects functional and competitive stem cells and is conducted as previously described (Harrison (1990) *Blood* 55:77-81).

Flow Cytometry

FITC-conjugated anti-mouse CD45.2 and anti-mouse C45.1 (BD Biosciences) are used to assay mouse donor cell chimerism of transplanted B6.BoyJ mice, whereas anti-human CD45 (FITC, clone 2D1; BD PharMingen) is used to assess human donor cell chimerism of NOD/SCID mice. CD34 (PE, clone 8G12), biotinylated Sca-1 developed with SA-PerCPCy5.5, lineage markers conjugated to APC (CD3, B220, Gr-1), and cKit-FITC antibodies are purchased from BD Biosciences. These antibodies are used to identify and tabulate human and murine stem cells.

Example 3

Murine Stem Cell Mobilization

C57Bl/6 mice are administered a pyrimidine Btk inhibitor through subcutaneous injection. Saline injections are used as the control. Dose response (0-50 mg/kg) and time response (0-24 hours) curves are done. Peripheral blood is collected from the mice and used for colony forming assays (ie, CFU-GM, BFU-E, and CFU-GEMM) for assessment of hematopoietic progenitors. Flow cytometry is used to count changes in HSC levels (Lin-Sca1+Kit+ cells).

Example 4

Homing Studies

Low-density mobilized with pyrimidine Btk inhibitor [N=10] versus saline control) peripheral blood from C57Bl/6 (CD45.2+) donor mice are transplanted via tail-vein injections into B6.BoyJ (CD45.1+) recipient mice [N=1-4/group]. The recipient mice are killed and the bone marrow harvested. The bone marrow from the recipient is phenotyped by flow cytometry to assess presence of CD45.2+ HSC (Lin-Sca1+Kit+).

Example 5

Long-Term Engraftment Studies

To assess mobilization of functional murine HSC, a competitive repopulating assay in mice is done. Donor cells from C57Bl/6 (CD45.2+) mice mobilized with pyrimidine Btk inhibitor (N=36) versus saline control (N=18) are administered to lethally irradiated B6.BoyJ (CD45.1+) mice (N=6/group). Bone marrow from nonirradiated B6.BoyJ (CD45.1+) serve as the competitor cells. The recipient mice are bled once monthly after transplant for up to 4 months to determine percentage of CD45.2+ CD45.1− peripheral blood leucocytes. Bone marrow from the B6.BoyJ (CD45.1+) recipient mice are used for a second transplantation experiment in B6.BoyJ (CD45.1+) mice. The second set of recipient mice are bled once monthly for up to 4 months to determine percentage of CD45.2+ CD45.1− peripheral blood leucocytes. Recipient mice are given a lethal dose of irradiation (950 cGy) before i.v. injection of donor cells.

Example 6

Human Stem Cell Mobilization

To evaluate the effect of pyrimidine Btk with and without G-CSF on stem cell mobilization, a human SCID repopulating cells assay is used (Dick et al (1997) *Stem Cells* 15:199-203). Healthy volunteers (N=4/group) receive (1) 5 daily injections of G-CSF (10 µg/kg); (2) 1 injection of Btk inhibitor (dose TBD) only on Day 5; or (3) 5 daily injections of G-CSF (10 µg/kg) plus 1 injection of Btk inhibitor (dose TBD) on Day 5. The subjects undergo apheresis on Day 6. $2.5 \times 10^6$ CD34+ cells are transplanted intravenously into NOS/SCID mice (N=3/group) conditioned with 300 cGy of total body irradiation. One day later, the bone marrow is harvested from the mice and the percentage of human cells determined by direct measurement of total human CD45+ cells.

Certain modifications and improvements will occur to those skilled in the art upon a reading of the foregoing description. It should be understood that all such modifications and improvements have been omitted herein for the sake of conciseness and readability but are properly within the scope of the following claims.

The invention claimed is:

1. A method for mobilizing hematopoietic stem and/or progenitor cells in a subject, comprising administering to said subject a pharmaceutical composition comprising a Bruton's Tyrosine Kinase (Btk) inhibitor comprising a pyrimidine ring in an amount effective to inhibit Bruton's Tyrosine Kinase and mobilize said progenitor cells into the peripheral blood of said subject.

2. The method of claim 1, wherein said Btk inhibitor is a compound selected from Formula I:

wherein:
La is $CH_2$, O, NH or S;
Ar is a substituted or unsubstituted aryl, unsubstituted phenyl, or a substituted or unsubstituted heteroaryl;
Y is a 4-, 5-, 6-, or 7-membered cycloalkyl ring, or
Y is a 4-, 5-, 6-, or 7-membered monocyclic nitrogen containing heterocycloalkyl ring; or
Y is an optionally substituted group selected from among alkyl, heteroalkyl, cycloalkyl, heterocycloalkyl, aryl, and heteroaryl; or
Y is selected from form the group consisting of azetidinyl, pyrrolidinyl, piperidinyl, and azepanyl;
Z is C(=O), OC(=O), NHC(=O), NRC(=O), C(=S), S(=O)$_x$, OS(=O)$_x$, NHS(=O)$_x$, where x is 1 or 2;
$R_7$ and $R_8$ are independently selected from among H, unsubstituted $C_1$-$C_4$alkyl, substituted $C_1$-$C_4$alkyl, $C_1$-$C_6$alkoxyalkyl, $C_1$-$C_8$alkylaminoalkyl, $C_1$-$C_4$alkyl (phenyl), unsubstituted $C_1$-$C_4$heteroalkyl, substituted $C_1$-$C_4$heteroalkyl, unsubstituted $C_3$-$C_6$cycloalkyl, substituted $C_3$-$C_6$cycloalkyl, unsubstituted $C_2$-$C_6$heterocycloalkyl, and substituted $C_2$-$C_6$heterocycloalkyl; or
$R_7$ and $R_8$ taken together form a bond;
$R_6$ is H, substituted or unsubstituted $C_1$-$C_4$-$C_4$alkyl, substituted or unsubstituted $C_1$-$C_4$heteroalkyl, $C_1$-$C_6$alkoxyalkyl, $C_1$-$C_g$alkylaminoalkyl, substituted or unsubstituted $C_3$-$C_6$cycloalkyl, substituted or unsubstituted aryl, substituted or unsubstituted $C_2$-$C_8$heterocycloalkyl, substituted or unsubstituted heteroaryl, $C_1$-$C_4$alkyl(aryl), $C_1$-$C_4$alkyl(phenyl), $C_1$-$C_4$alkyl(heteroaryl), $C_1$-$C_4$alkyl($C_3$-$C_8$cycloalkyl), or $C_1$-$C_4$alkyl($C_2$-$C_8$heterocycloalkyl), or $C_1$-$C_8$alkylaminoalkyl;
R is H, or $C_1$-$C_6$alkyl and
pharmaceutically acceptable solvates or pharmaceutically acceptable salts thereof.

3. The method of claim 1, wherein said Btk inhibitor is a compound selected from Formula II:

wherein:
Ra, Rb, Rc, Rd, and Re, are each independently selected from H, F, Cl, Br, I, —CN, —$SR_2$, —$OR_3$, $CO_2R_3$; or
Ra, or Rb together with one of Rc, Rd and Re, and the carbon atoms to which they are attached form an epoxide;
wherein Ra, Rb, Rc, Rd, and Re, cannot all be H;
$R_2$ is selected from H, methyl, ethyl, n-propyl, iso-propyl, n-butyl, iso-butyl, tert-butyl, a cysteinyl, a glutathionyl, and $C_1$-$C_4$alkyl;
$R_3$ is selected from H, $C_1$-$C_4$alkyl, phenyl, or benzyl; and pharmaceutically acceptable solvates or pharmaceutically acceptable salts thereof.

4. The method of claim 1, wherein said Btk inhibitor is a compound selected from Formula III:

wherein;
La is O or S;
Ar is an unsubstituted phenyl;
Y is a 4-, 5-, 6-, or 7-membered cycloalkyl ring, or
Y is a 4-, 5-, 6-, or 7-membered monocyclic nitrogen containing heterocyclic ring;
Z is C(=O), OC(=O), NHC(=O), S(=O)$_x$, or NHS (=O)$_x$, where x is 2;
$R_8$ is H; $R_7$ is H, unsubstituted $C_1$-$C_4$ alkyl, $C_1$-$C_6$alkoxyalkyl, $C_1$-$C_8$alkylaminoalkyl, or $C_1$-$C_4$alkyl(phenyl); or $R_7$ and $R_8$ taken together form a bond;

$R_6$ is H, unsubstituted $C_1$-$C_4$ alkyl, $C_1$-$C_6$alkoxyalkyl, $C_1$-$C_8$alkylaminoalkyl, or $C_1$-$C_4$alkyl(phenyl); and pharmaceutically acceptable solvates or pharmaceutically acceptable salts thereof.

5. The method according to claim 1, wherein said subject has impaired hematopoiesis.

6. The method according to claim 5, wherein said administering step is performed subsequent to a myelosuppressive or myeloablative treatment of said subject.

7. The method according to claim 6, wherein said myelosuppressive or myeloablative treatment comprises chemotherapy.

8. The method according to claim 5, wherein said administering step is performed after accidental radiation exposure to said subject.

9. The method according to any one of claims 1-8, said method further comprising the simultaneous or sequential administration of an additional mobilizing agent selected from the group consisting of granulocyte-macrophage colony stimulating factor (GM-CSF), Interleukin-1 (IL-1), Interleukin-3 (IL-3), Interleukin-8 (IL-8), PIXY-321 (GM-CSF/IL-3 fusion protein), macrophage inflammatory protein, stem cell factor, plerixafor, thrombopoietin, growth related oncogene, and combinations thereof.

10. A method for mobilizing hematopoietic stem and/or progenitor cells in a subject, comprising administering to said subject a pharmaceutical composition comprising a Bruton's Tyrosine Kinase (BTK) inhibitor comprising a pyrimidine ring in an amount effective to inhibit Bruton's Tyrosine Kinase and mobilize said progenitor cells into the peripheral blood of said subject, wherein the BTK inhibitor is 1-[(3R)-3-[4-amino-3-(4-phenoxyphenyl)pyrazolo[3,4-d]pyrimidin-1-yl]piperidin-1-yl]prop-2-en-1-one.

11. A method of obtaining hematopoietic stem and/or progenitor cells from a subject comprising (a) mobilizing said hematopoietic stem and/or progenitor cells according to the method of any one of claims 1-4 and 10; and (b) harvesting said cells.

12. The method according to claim 11, wherein said cells are harvested by apheresis.

13. A method of providing hematopoietic cells to a patient in need thereof comprising introducing cells obtained by a method according to claim 11 or 12 to said patient.

14. The method according to claim 13, wherein said patient is undergoing bone marrow transplantation.

15. The method according to claim 14, wherein said subject and said patient are histocompatible.

16. The method according to claim 15, wherein said subject and said patient are syngeneic.

17. The method according to claim 15, wherein said subject and said patient are allogeneic.

18. The method according to any one of claims 13-17, wherein said method comprises culturing the obtained cells are cultured to enrich and/or differentiate the hematopoietic stem and/or progenitor cells prior to introducing the cells into the patient.

19. The method of claim 18, wherein the cells are enriched for or differentiated into myeloid cells.

20. The method of claim 13, wherein the cells are enriched for or differentiated into lymphoid cells.

21. The method of claim 13, wherein the cells are enriched for or differentiated into NK cells.

22. The method of claim 1, wherein the mobilizing Btk inhibitor is either reversible or irreversible.

* * * * *